United States Patent [19]

Wolf

[11] 4,255,353

[45] Mar. 10, 1981

[54] SULFINYL-BIS CARBAMOYL FLUORIDES

[75] Inventor: Anthony D. Wolf, Newark, Del.

[73] Assignee: E. I. Du Pont de Nemours and Company, Wilmington, Del.

[21] Appl. No.: 87,078

[22] Filed: Oct. 22, 1979

[51] Int. Cl.$^3$ ............................................. C07C 125/03
[52] U.S. Cl. ................... 260/544 C; 424/300
[58] Field of Search .................. 260/544 C; 71/100; 424/300

[56] References Cited

U.S. PATENT DOCUMENTS

| | | | |
|---|---|---|---|
| 3,301,894 | 1/1967 | Ottmann et al. | 260/544 C |
| 3,598,859 | 8/1971 | Yates et al. | 71/100 |
| 4,004,031 | 1/1977 | Drabek | 424/327 |
| 4,127,605 | 11/1978 | Hay | 260/544 C |
| 4,151,353 | 4/1979 | Thurman | 260/544 C |

FOREIGN PATENT DOCUMENTS

| | | | |
|---|---|---|---|
| 717705 | 1/1969 | Belgium | 260/544 C |
| 848912 | 5/1977 | Belgium | 260/544 C |
| 2254313 | 8/1977 | Fed. Rep. of Germany | 260/544 C |

*Primary Examiner*—James H. Reamer

[57] ABSTRACT

Sulfinyl-bis carbamoyl fluorides, such as N,N'-sulfinyl-bis[N-methylcarbamoyl fluoride], useful as intermediates in the preparation of insecticides.

2 Claims, No Drawings

SULFINYL-BIS CARBAMOYL FLUORIDES

BACKGROUND OF THE INVENTION

This invention pertains to bis-carbamoyl fluorides which are useful as intermediates for the preparation of agricultural chemicals particularly insecticides.

Belgian Pat. No. 717,705 discloses carbamic acid fluorides useful as insecticides, fungicides and acaricides of the formula

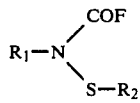

where $R_1$ and $R_2$ represent various defined substituents

SUMMARY OF THE DISCLOSURE

The present invention relates to novel intermediates of Formula I useful for preparation of insecticides

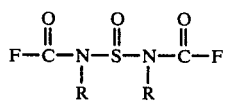

wherein
R is $C_1$–$C_3$ alkyl.

Specifically preferred for the ease of synthesis is the compound of Formula I wherein R is $CH_3$.

PREPARATION

The compounds of Formula I can be prepared as shown in the following schematic:

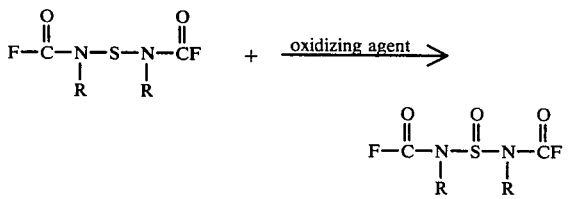

A thio bis-carbamoyl fluoride (described in Belgian Pat. No. 717,705) is treated with at least one equivalent of an appropriate oxidizing agent, such as m-chloroperbenzoic acid or peracetic acid. The reaction is carried out at a temperature in a range from −10° to +60° C., in a suitable solvent, such as methylene chloride or chloroform. After a suitable reaction time, such as 0.5 to 72 hours, the reaction mixture is washed preferably with water. Unreacted oxidant is removed and use of sodium bisulfite is suitable for this purpose. The product is dried, for example, by washing with saturated sodium chloride solution. The crude product is isolated by removing the solvent, e.g. by distillation or evaporation. The crude intermediate product can be used directly or it can be further purified by usual techniques such as crystallization.

The intermediate compounds of Formula I are useful for preparation of insecticides including compounds with this utility within the disclosure of concurrently filed Application Ser. No. 087,079. These compounds are of Formula II and are prepared in accordance with the following schematic.

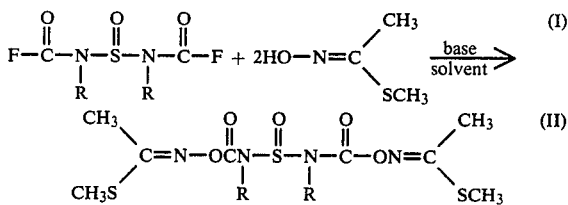

where R is as previously defined and is $C_1$–$C_3$ alkyl.

A sulfinyl-bis carbamoyl fluoride I is reacted with S-methyl N-hydroxythioacetimidate in the presence of a suitable base, e.g., a tertiary amine such as triethylamine, pyridine, or trimethylamine. Some examples of suitable solvents for this reaction include tetrahydrofuran, methylene chloride, dimethylformamide and acetonitrile. The reaction is carried out at temperature between −10° and +80° C. for a period of 0.5 to 72 hours. The product is isolated by pouring the crude reaction mixture into water, followed by extraction with a suitable solvent such as methylene chloride or diethyl ether. The organic extract of the product is concentrated by distillation or evaporation on a rotary evaporator. The product can be further purified by usual techniques such as crystallization.

Example 1 describes an illustrative procedure for preparation of an intermediate compound of Formula I; Example 2 describes an illustrative procedure for an insecticidal compound of Formula II. All parts are be weight and temperatures in degrees centigrade unless otherwise specified.

EXAMPLE 1

N,N'-sulfinylbis[N-methylcarbamoyl fluoride]

7.8 g Of N,N'-thiobis[N-methylcarbamoyl flouride], 13.0 g of m-chloroperoxybenzoic acid and 300 ml of methylene chloride were stirred at room temperature for 24 hours, after which the crude reaction mixture was filtered and washed successively with 100 ml of ice water, 100 ml 25% sodium bisulfite solution and 100 ml saturated sodium chloride. The organic layer was dried over anhydrous mangesium sulfate and then concentrated on a rotary evaporated. 12.9 g of crude product was obtained.

EXAMPLE 2

Dimethyl N,N'[sulfinylbis[(methylimino)-carbonyloxy]]bis[ethanimidothioate]

1.5 g of N,N'-Thiobis[N-methylcarbamoyl flouride], and 1.7 g of m-chloroperoxybenzoic acid (85%) and 25 ml of methylene chloride were combined and stirred 72 hours at room temperature to form the intermediate N,N'-sulfinylbis[N-methylcarbamoyl fluoride]. The crude reaction mixture was filtered to remove benzoic acid. The volume of the reaction solution was brought to about 50 ml by addition of methylene chloride.

To the crude N,N'-sulfinylbis[N-methylcarbamoyl fluoride] formed in the above reaction is added 2.3 g of pyridine and 2.1 g of S-methyl-N-hydroxythioacetimidate. The reaction mixture was stirred at room temperature for 24 hours. The crude reaction mixture containing the product was poured into 200 ml of water. The methylene chloride layer was separated. The water layer was extracted with three 100 ml portions of methylene chloride. The organic extracts were combined and dried with anhydrous sodium sulfate. The solvent was removed on a rotary evaporator to leave the crude product which was purified by recrystallization from ethanol to yield 0.5 g of white solid with m.p. of 136°.
What is claimed is:
1. A compound of the formula
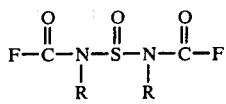
where R is $C_1$–$C_3$ alkyl.
2. The compound of claim 1 of the formula
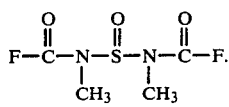
* * * * *